US008408043B2

(12) United States Patent
Stehle et al.

(10) Patent No.: US 8,408,043 B2
(45) Date of Patent: Apr. 2, 2013

(54) METHOD AND DEVICE FOR MEASURING THE AMOUNT OF A GAS IN A SEALED LIQUID CONTAINER

(75) Inventors: Gerard Stehle, Machilly (FR); Eric Studemann, Geneva (CH); Eric Michaud, Bonne (FR); Olivier Fraternale, Vernier (CH)

(73) Assignee: Hach Lange Sarl, Vesenaz (CH)

( * ) Notice: Subject to any disclaimer, the term of this patent is extended or adjusted under 35 U.S.C. 154(b) by 458 days.

(21) Appl. No.: 12/682,979

(22) PCT Filed: Oct. 16, 2007

(86) PCT No.: PCT/IB2007/003079
§ 371 (c)(1),
(2), (4) Date: Apr. 14, 2010

(87) PCT Pub. No.: WO2009/050530
PCT Pub. Date: Apr. 23, 2009

(65) Prior Publication Data
US 2010/0236320 A1    Sep. 23, 2010

(51) Int. Cl.
*G01N 33/18*    (2006.01)
(52) U.S. Cl. ........................................................ 73/19.1
(58) Field of Classification Search .................. 73/19.01, 73/19.06, 19.1, 863.85
See application file for complete search history.

(56) References Cited

U.S. PATENT DOCUMENTS

| 3,203,248 | A | * | 8/1965 | Stutler et al. ............... 73/863.85 |
| 5,220,513 | A |  | 6/1993 | Seiden et al. |
| 5,426,593 | A |  | 6/1995 | Seiden et al. |
| 5,556,902 | A | * | 9/1996 | Shouji et al. .................. 516/117 |
| 5,604,297 | A |  | 2/1997 | Seiden et al. |

FOREIGN PATENT DOCUMENTS
WO    9967632 A1    12/1999

OTHER PUBLICATIONS

Search Report and Written Opinion in PCT/IB2007/003079, Jul. 25, 2008.

* cited by examiner

*Primary Examiner* — Peter Macchiarolo
*Assistant Examiner* — Jamar Ray
(74) *Attorney, Agent, or Firm* — Bacon & Thomas, PLLC

(57) ABSTRACT

A method for measuring an amount of a determined gas, particularly oxygen, in a sealed container of a liquid, such as a carbonated beverage, in which a gas mixture is dissolved, involves piercing the sealed container, releasing the gas mixture contained in the pierced container, measuring an amount of the determined gas in the released gas mixture, determining, based on the measuring, an initial amount of the determined gas in the sealed container, and injecting an anti-foam agent into the pierced container before and/or during the gas releasing step.

19 Claims, 5 Drawing Sheets

METHOD AND DEVICE FOR MEASURING THE AMOUNT OF A GAS IN A SEALED LIQUID CONTAINER

FIELD OF INVENTION

The present invention relates to a method and a device for measuring an amount of a gas, particularly oxygen, in a sealed container of a liquid in which a gas mixture is dissolved. The liquid is typically a carbonated beverage.

BACKGROUND

Three main gases are generally present in a carbonated beverage: carbon dioxide ($CO_2$), oxygen ($O_2$) and nitrogen ($N_2$). Carbon dioxide is the desired gas. Oxygen is undesired.

Direct measurement of the amount of a gas in a liquid phase is possible but has some drawbacks. One of them is the necessity for shaking the liquid before the measurement until a state of equilibrium between the liquid phase and the gaseous phase is obtained. Another drawback is that, to perform the measurement, the liquid is to be passed into various sensors and this may affect the reliability of the sensors. This is why another method is proposed in U.S. Pat. Nos. 5,220,513, 5,426,593 and 5,604,297 for measuring the amount of a determined gas, particularly oxygen, in a sealed liquid container, in which method the sealed liquid container is pierced, the pierced container is degassed to release the gases from the liquid phase, using ultrasounds or other degassing means, the released gases are passed into a test chamber, and the amount of the determined gas in the released gases in the test chamber is measured with a specific sensor. However, a problem with that method is that degassing causes foam to be formed at the liquid-gas interface, especially in carbonated beverages such as beer, which foam may wet the probe of the sensor and thus affect the measurement. To remedy this problem, it is proposed in the above-mentioned patents to use a foam chamber between the liquid container and the test chamber to absorb the foam. This solution however has several drawbacks. The use of such a foam chamber increases the risk of contaminating the gas mixture extracted from the liquid with oxygen. Indeed, due to its much larger size than the conduits of the gas circuit, a chamber is more likely to house contaminants that will resist purging. Oxygen that remains in the chamber after the gas circuit has been purged may affect the measurement. Another drawback is that with such a foam chamber the wait time before which the measurement can be made, after piercing the sealed liquid container, may be long because it must be waited until the foam has fallen down in the foam chamber.

SUMMARY

The present invention aims at remedying the above-mentioned drawbacks and provides, to this end, a method for measuring an amount of a determined gas in a sealed container containing a liquid in which a gas mixture is dissolved, comprising the steps of:
  piercing the sealed container,
  releasing the gas mixture from the pierced container,
  measuring an amount of the determined gas in the released gas mixture,
  determining, based on said measuring, an initial amount of the determined gas in the sealed container,
characterised by further comprising the step of injecting an anti-foam agent into the pierced container before and/or during the gas mixture releasing step.

The present invention also provides a device for measuring an amount of a determined gas in a sealed container containing a liquid in which a gas mixture is dissolved, comprising:
  means for piercing the sealed container,
  means for releasing the gas mixture from the pierced container,
  means for measuring an amount of the determined gas in the released gas mixture,
  means for determining, based on said measuring, an initial amount of the determined gas in the sealed container,
characterised by further comprising means for injecting an anti-foam agent into the pierced container.

BRIEF DESCRIPTION OF THE DRAWINGS

Other features and advantages of the present invention will be apparent upon reading the following detailed description of a preferred embodiment made with reference to the appended drawings in which.

DETAILED DESCRIPTION OF VARIOUS EMBODIMENTS OF THE DISCLOSURE

In the following, the term "amount" is to be understood in a broad sense, as referring to any amount-related magnitude, for example mass, volume or partial pressure.

Figure 1:
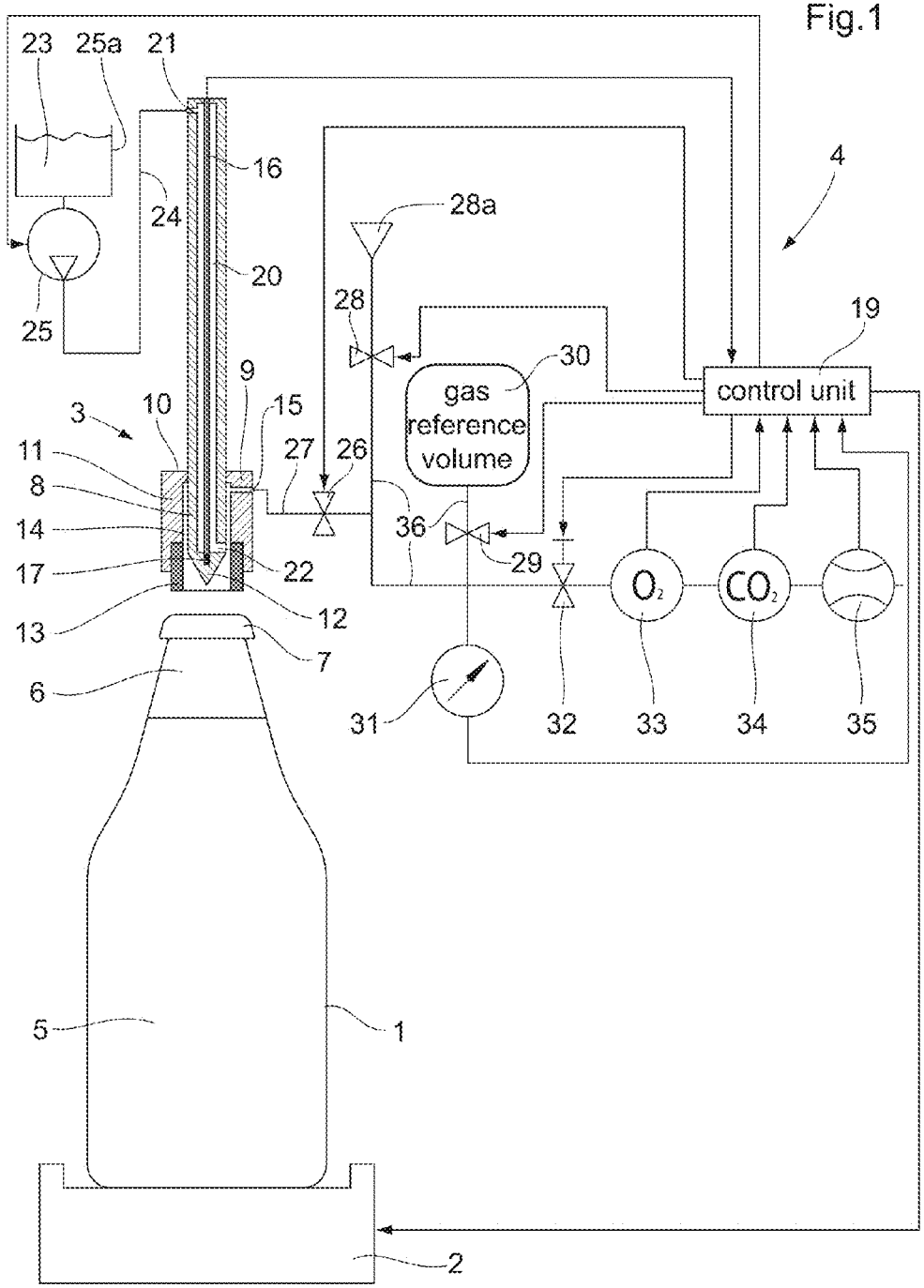
FIGS. 1 to 4 diagrammatically show the device according to the invention at different stages of the method according to the invention.

With reference to FIG. 1, a device according to the invention, for measuring the amount of oxygen in a sealed liquid container 1, i.e. typically a bottle or can of a carbonated beverage such as beer, comprises a support 2 for supporting the liquid container 1, a piercing mechanism 3 for piercing the liquid container 1 and a gas circuit 4 connected to the piercing mechanism 3 and including conduits and organs for measuring the amount of oxygen and other gases in the container 1.

The liquid contained in the container 1 is designated by reference numeral 5. Above the liquid 5 is provided a space 6 occupied only by gases. Such a space is commonly referred to as the headspace of the container. The container 1 is sealed by a cap 7. The support 2 encases a known-type vibrating, e.g. ultrasonic, device (not shown) for shaking the liquid 5 inside the container 1 and thus extracting the gases from the liquid 5. In the following, the vibrating device will also be designated by reference numeral 2.

The piercing mechanism 3 comprises a needle 8 which extends vertically above the cap 7 of the container 1 and which is moveably mounted within a sleeve member 9. The sleeve member 9 has an upper wall 10 with a hole through which the needle 8 passes in a sealed manner, and a cylindrical wall 11 which extends downwards from the upper wall 10 and surrounds the needle 8. The lower end of the sleeve member 9, opposite the upper wall 10, is open to leave the tip 12 of the needle 8 free. The needle 8 is represented in FIG. 1 in its retracted position. From this retracted position, the needle 8 may be moved longitudinally downwards to pierce the container cap 7. The needle 8 and the sleeve member 9 may also be moved together downwards and upwards, as will be apparent later in this description. The open end of the sleeve member 9 is fitted with a cylindrical rubber gasket 13. A thin annular free space 14 is provided between the needle 8 and the respective internal walls of the sleeve member 9 and of the gasket 13 to define a gas path. This free space 14 communicates at one side with the open end of the sleeve member 9 and at the other side with a through hole 15 provided in the cylindrical wall 11.

The needle 8 is hollow and accommodates in its internal space a tube 16 which extends in the longitudinal direction of the needle 8 and through which electrical wires (not shown) pass. The electrical wires are connected at one end to a temperature sensor 17 situated in the tip 12 of the needle 8 and at their other end to a control unit 19, typically a processor, which may thus receive temperature-indicative signals from the temperature sensor 17. A cylindrical annular free space 20 is provided between the tube 16 and the internal wall of the needle 8. This free space 20 communicates with a first through hole 21 provided in the wall of the needle 8 at the upper end of the needle 8 and with a second through hole 22 provided in the wall of the needle 8 at the lower end of the needle 8, to constitute a path for an anti-foam agent 23. The first through hole 21 communicates via a conduit 24 with a pump 25 which is connected to a reservoir 25a containing the anti-foam agent 23.

The gas circuit 4 connected to the piercing mechanism 3 comprises a first valve 26 connected via a gas conduit 27 to the through hole 15 in the cylindrical wall 11 of the sleeve member 9, a second valve 28 connected to a purge gas, e.g. $CO_2$, inlet 28a, a third valve 29 connected to a gas reference volume 30, a pressure sensor 31, a fourth valve 32 and, downstream of the fourth valve 32, an $O_2$ sensor 33, a $CO_2$ sensor 34 and a flowmeter 35. Conduits 36 interconnect the various elements of the gas circuit 4. The pressure sensor 31 measures the total gas pressure in the gas circuit 4. The $O_2$ and $CO_2$ sensors 33, 34 and the flowmeter 35 are at the atmospheric pressure. The $O_2$ sensor 33 measures the partial pressure of $O_2$. The $CO_2$ sensor 34 measures the purity of the $CO_2$, more precisely the percentage in volume of $CO_2$ in the gas mixture released from the container 1 through the valve 32. Preferably, the valve 32 is regulated by the flowmeter 35, in a manner that is known per se, so that the gas flow rate be constant.

The vibrating device 2, the pump 25, the movements of the piercing mechanism 3 and the valves 26, 28, 29 and 32 are all controlled by the control unit 19 according to an automatic sequence which is described below. The sensors 31, 33, 34 and the flowmeter 35 are also connected to the control unit 19, to provide this latter with measurement signals enabling it to perform various calculations which are described below.

Operation of the device according to the invention will now be described.

In a first step (FIG. 1), the valves 26, 28 and 29 are opened (the valve 32 remaining closed) so that the purge gas flowing from inlet 28a passes into the conduits 36 of the gas circuit 4 and into the gas path 14 of the needle mechanism 3 to purge them. At the end of this step, the volume 30 is filled with the purge gas and the valve 29 is closed to enclose the purge gas within the volume 30 while the pressure measured by the sensor 31 is stored. This stored pressure is the pressure of the enclosed purge gas. It will be used at the end of the sequence to calibrate the flowmeter 35.

Figure 2:
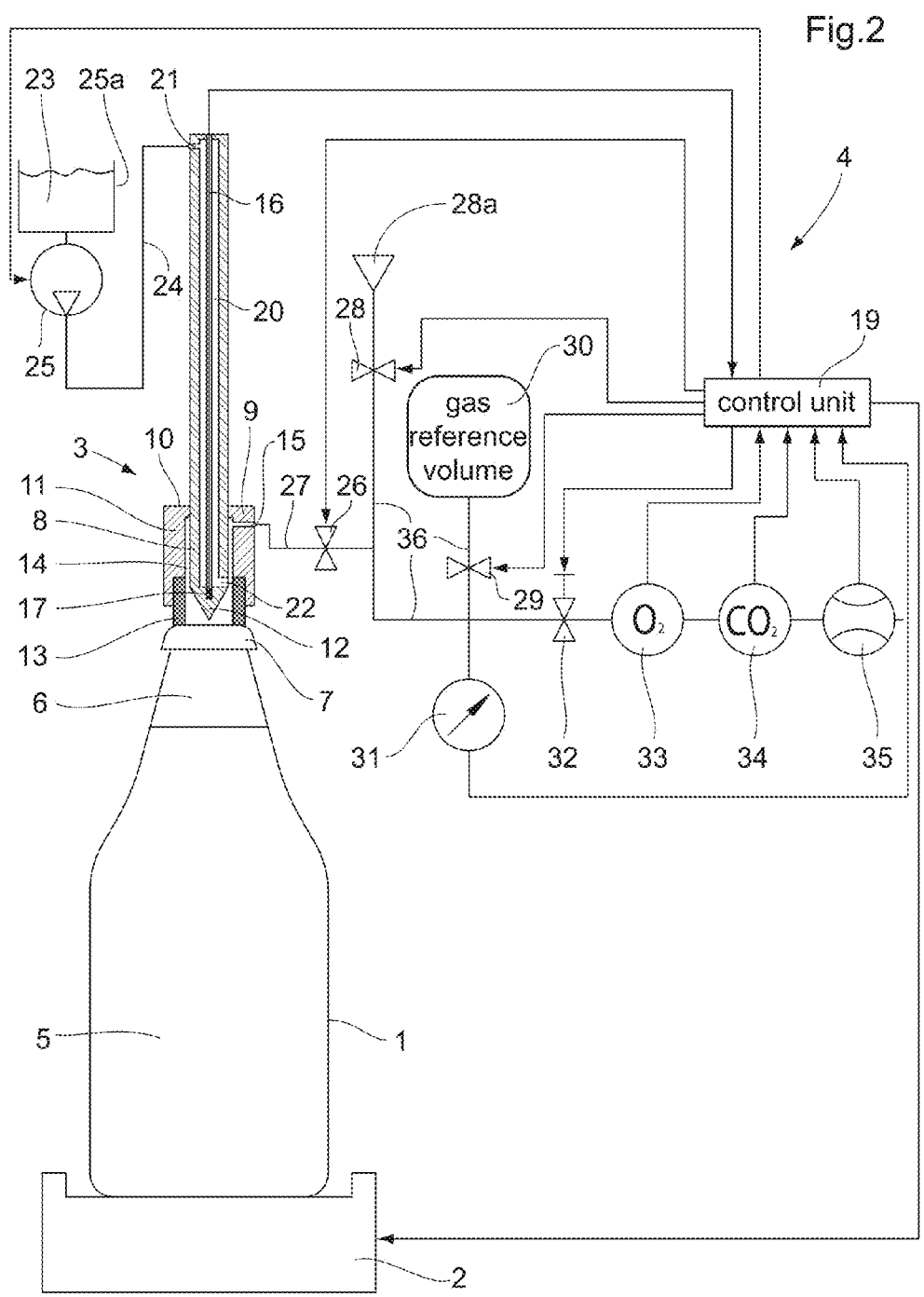

In a second step (FIG. 2), the needle 8 and the sleeve member 9 together are moved downwards while the gas path 14 is purged with purge gas flowing from the inlet 28a until the rubber gasket 13 contacts the container cap 7 in a sealed manner. At the moment when sealed contact between the gasket 13 and the cap 7 is established, a quick change of the pressure measured by the pressure sensor 31 occurs. As soon as this quick change is detected, the valve 28 is closed.

Figure 4:
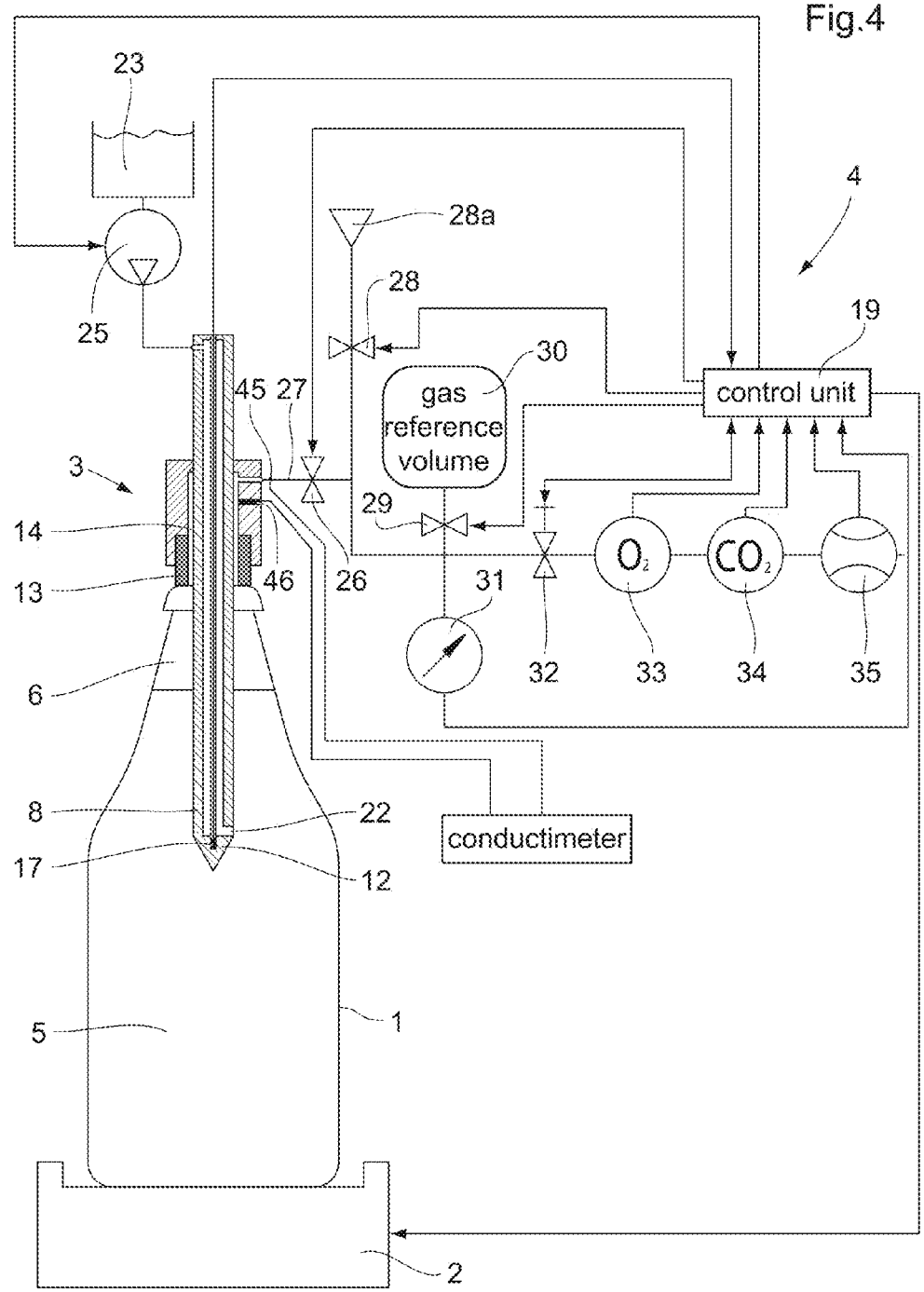
Figure 5:
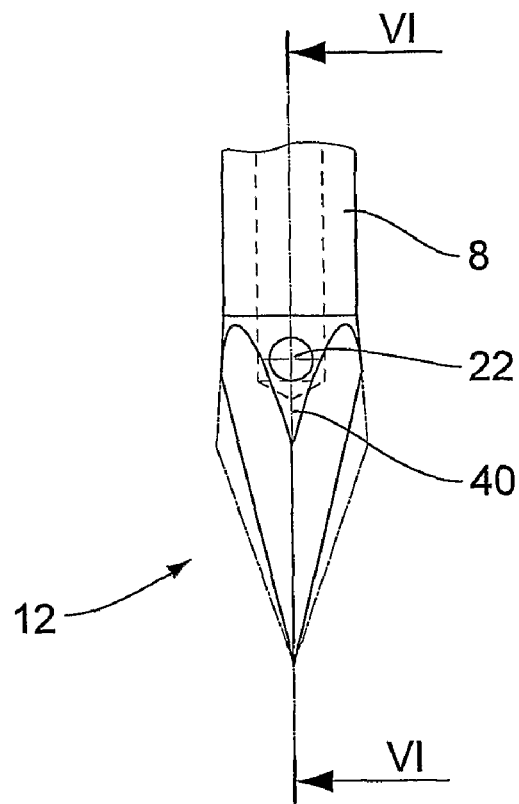
FIGS. 5 and 6 respectively show in front view and in section view taken along the line VI-VI of FIG. 5, the tip of a piercing needle of the device according to the invention.
Figure 6:
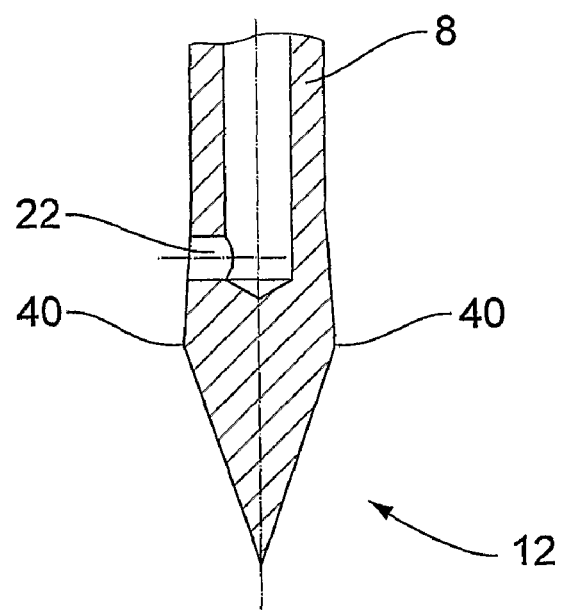

In a third step (FIG. 3), the needle 8 is moved downwards relative to the sleeve member 9 and the liquid container 1 so that the cap 7 is pierced and the tip 12 of the needle 8 is plunged into the headspace 6. The tip 12 of the needle 8 does not have a perfectly round cross-section but rather has radial protuberances (not visible in FIGS. 1-4) which the remainder of the needle 8 does not have, in order to create paths at the periphery of the hole pierced into the cap 7 permitting the inside of the container 1 to communicate with the gas path 14 in the piercing mechanism 3 and thus with the gas circuit 4, despite the needle 8 passing through the pierced hole. An example of a tip shape having such radial protuberances 40 is shown in FIGS. 5 and 6. During this third step, the purge gas pressure in the gas path 14 and the gas circuit 4 is greater than the gas pressure inside the container 1 and thus prevents the gases contained in the container 1 from getting out.

Figure 3:
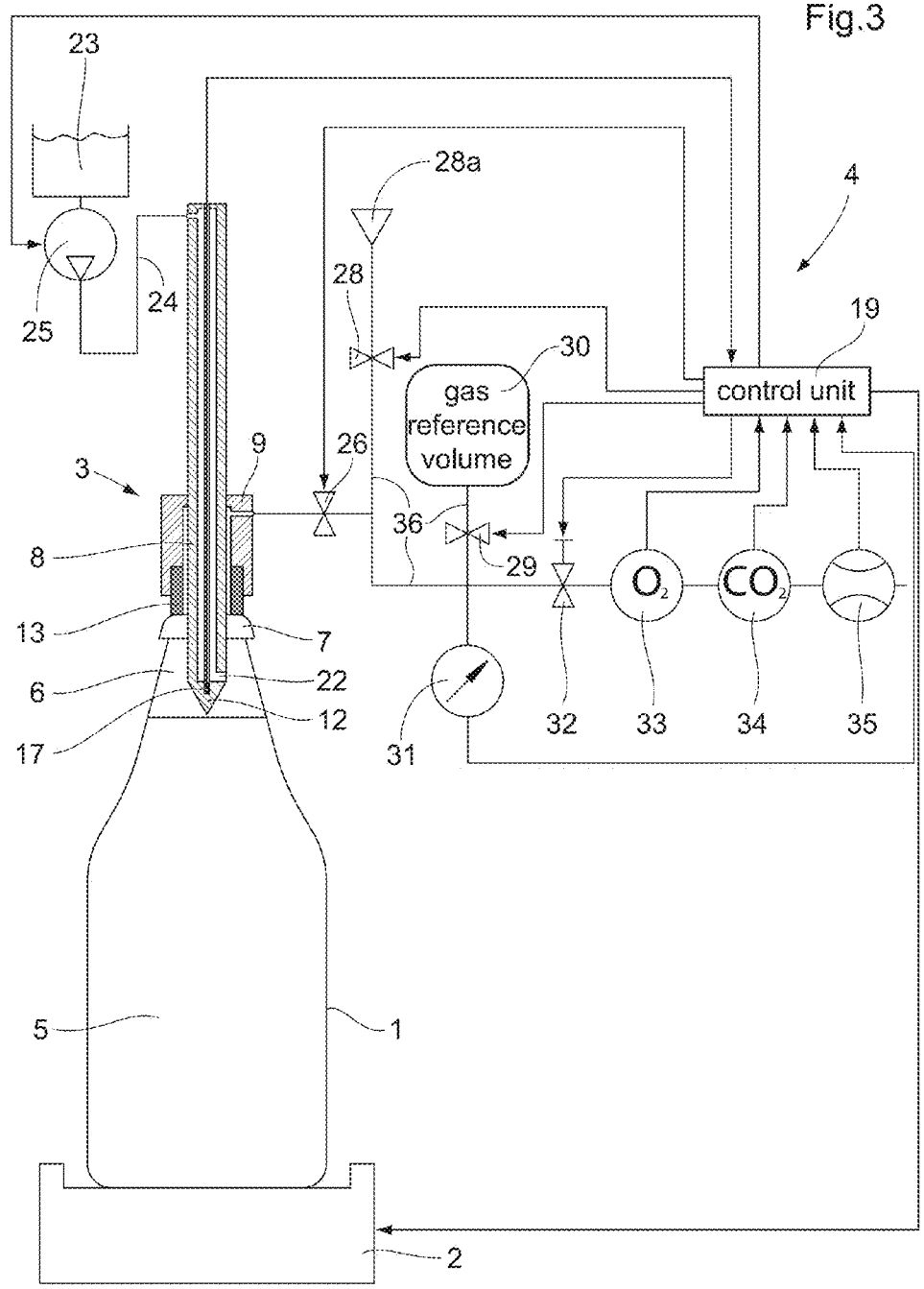

In a fourth step, with the needle 8 in its position shown in FIG. 3, one or several drops of the anti-foam agent 23 are injected into the headspace 6 by the pump 25 through the hollow needle 8. Various types of commercially available anti-foam agents can be used in this invention. However, a preferred anti-foam agent includes a suspension of a silica powder in a silicone oil/water emulsion. The one or several drops of the anti-foam agent deposit onto the gas-liquid interface in the container 1 to destroy any foam already formed by intentionally or unintentionally shaking the container 1 before placing it onto the support 2 and any foam formed in the subsequent steps of the present process as described below, so that said foam does not reach the sensors 31, 33 and 34 and, thus, does not affect the measurements. It will be appreciated that the use of such an anti-foam agent obviates the need for a foam absorbing chamber.

A fifth step consists in measuring the amount of oxygen in the headspace 6. To this effect, after a determined time period, sufficiently long for any foam to have disappeared in the container 1, the valve 32 is opened to start the degassing of the headspace 6, i.e. the gas mixture contained in the headspace 6 flows towards the $O_2$ sensor 33 through the gas path 14 and the gas circuit 4. The partial $O_2$ pressure measured by the sensor 33 increases until it reaches a ceiling value. The valve 32 is closed at an instant when the ceiling value is considered to be reached. Based on this measured ceiling value of the partial $O_2$ pressure, on the known volume of the headspace 6 and on the perfect gas law, the initial $O_2$ volume in the headspace 6, i.e. the $O_2$ volume in the headspace 6 before piercing the cap 7, is determined. During this fifth step, an integral over time of the product of the gas flow rate measured by the flowmeter 35 and the partial $O_2$ pressure measured by the sensor 33 is calculated. The purpose of this integral calculation is explained below in the description of the seventh step. Moreover, the amount of $CO_2$ that escapes through the valve 32 during this fifth step is also calculated, using the values measured by the $CO_2$ sensor 34 and the value(s) of the gas flow rate.

In a sixth step, the initial amount of $CO_2$ in the container 1 is measured. To this effect, the vibrating device 2 is activated while the gas flow remains stopped (valve 32 closed). Activation of the vibrating device 2 causes foam to be formed in the container 1 but the foam is destroyed by the anti-foam agent 23 as it is being formed. An equilibrium pressure and an equilibrium temperature are reached in the container 1, corresponding to a state of equilibrium between the liquid and gaseous phases. These equilibrium pressure and temperature are measured, respectively, by the pressure sensor 31 and by the temperature sensor 17. In this sixth step, the needle 8 is so positioned that its tip 12 and hence the temperature sensor 17 are plunged in the liquid 5, as shown in FIG. 4. By means of formulas that are known to the skilled person, and using the measured equilibrium pressure and temperature, the mass of $CO_2$ in the liquid 5 and the mass of $CO_2$ in the headspace 6 at equilibrium are determined. The known formulas however involve the total pressure as measured in the present invention by the pressure sensor 31. For greater accuracy, the present invention replaces in the known formulas the total equilibrium pressure by the product of the total equilibrium pressure and the percentage of $CO_2$ as measured by the $CO_2$ sensor 34 after re-opening of the valve 32, in the seventh step described below. The initial total mass of $CO_2$ in the container 1 is equal to the sum of said mass of $CO_2$ in the liquid 5 at equilibrium, said mass of $CO_2$ in the headspace 6 at equilibrium and the mass of $CO_2$ that escaped during the fifth step. The initial mass of $CO_2$ in the headspace 6 may be calculated using the pressure and the temperature respectively measured by the sensors 31 and 17 at the instant when the degassing is started (opening of valve 32 in the fifth step), the measured percentage of $CO_2$ and the headspace volume. The initial mass of $CO_2$ in the liquid 5 may be deduced by subtracting the initial mass of $CO_2$ in the headspace 6 from the initial total mass of $CO_2$ in the container 1. An advantage of the present invention is that the operation of equilibrating the liquid and gaseous phases to determine the amount of $CO_2$ in the container 1 is performed as of an instant when the pressure in the container 1 is relatively low (during the fifth step, indeed, the pressure decreases as gases flow out of the container 1). The gap between that pressure and the equilibrium pressure is thus high. This results in the equilibrium being reached more rapidly and, accordingly, in more precise values of the equilibrium pressure and temperature being obtained.

A seventh step consists in measuring the initial total amount of oxygen in the container 1. The valve 32 is re-opened while the vibrating device 2 is active to degas not only the headspace 6 but also the liquid 5. The gases dissolved in the liquid 5 escape from the latter and mix with the gases contained in the headspace 6 to flow towards the $O_2$ sensor 33. The initial total volume of oxygen in the container 1 is determined by calculating an integral over time of the product of the gas flow rate measured by the flowmeter 35 and the partial $O_2$ pressure measured by the sensor 33, and by adding to the result obtained the integral calculated in the fifth step. Calculating an integral over time of the product of the gas flow rate and the partial $O_2$ pressure, as is done in this invention, enables an accurate value of the initial total amount of $O_2$ in the container 1 to be obtained.

Using the values provided during the fifth and seventh steps by the $CO_2$ purity sensor 34, the initial amount of air (oxygen+nitrogen) and of nitrogen in the container 1 may be calculated.

As already explained, an advantage of this invention is that the $O_2$ and $CO_2$ measurements are not perturbed by foam reaching the sensors 33, 34. Generally, it will be sufficient that the anti-foam agent 23 be injected into the container 1 prior to starting the degassing of the container 1. However, the invention does not exclude injecting the anti-foam agent 23 also or only during degassing. One condition to be fulfilled to avoid foam getting out of the container 1 is that the flow rate is not too high. With too high a flow rate, indeed, the anti-foam agent 23 might not have sufficient time to destroy the foam as it is being formed.

Advantageously, a safety device is provided in the invention to detect any unexpected foam overflow. This safety device includes first and second electrical contacts 45, 46 located for example in the conduct 27, upstream of the valve 26, and in the gas path 14 of the piercing mechanism 3, respectively, as shown diagrammatically in FIG. 4. These electrical contacts 45, 46 are connected to an electrical circuit (not shown) including a conductimeter. The conductimeter measures the conductivity or resistance between the first and second contacts 45, 46. Since the conductivity of foam is high, if foam reaches the first contact 45, the conductivity between the contacts 45, 46 will rise fast. Such a rise is detected, which causes the valve 32 to be closed and the purge inlet valve 28 to be opened so as to push the foam back into the container 1, keeping the gas flow path dry and clean.

From time to time, calibration of the flowmeter 35 is required. Such a calibration may be performed by opening the valves 29 and 32 so that the gas contained in the reference volume 30 at a known pressure escapes. Measurement of the drop of the pressure measured by the sensor 31 (with respect to the known, initial pressure of the gas in the volume 30) in a given time interval permits calculating the flow rate. The calculated flow rate is compared with the flow rate measured by the flowmeter 35 and, if necessary, a correction factor is applied to the flowmeter 35.

The present invention has been described above by way of example only. It should be clear that modifications can be made without departing from the scope of the appended claims. In particular, the sequence of the measurements may be changed. For example, the measurement of the amount of $O_2$, more precisely the measurement of the amount of $O_2$ in the headspace 6 and the total amount of $O_2$ in the sealed container 1, could be carried out in one step, after the measurement is of the amount of $CO_2$. Other modifications of the invention could consist in adding further sensors, such as a sensor for detecting the amount of alcohol and/or infrared spectroscopy sensors for detecting other volatile compounds dissolved in the liquid 5.

The invention claimed is:

1. A method for measuring an amount of a determined gas in a sealed container containing a liquid in which a gas mixture is dissolved, comprising the steps of:
   piercing the sealed container;
   releasing the gas mixture from the pierced container;
   measuring an amount of the determined gas in the released gas mixture;
   determining, based on said measuring, an initial amount of the determined gas in the sealed container; and
   injecting an anti-foam agent into the pierced container before, during, or before and during the gas mixture releasing step,
   wherein the injecting step comprises passing the anti-foam agent through a path provided within a piercing member for piercing the sealed container to an opening of said piercing member situated close to a piercing tip of said piercing member.

2. The method according to claim 1, wherein said anti-foam agent comprises a suspension of silica powder into a silicone oil/water emulsion.

3. The method according to claim 1, wherein the gas mixture releasing step comprises a first step comprising releasing the gas mixture from a headspace of the pierced container, the measuring step comprises a first step comprising measuring an amount of the determined gas in the gas mixture released from the headspace, and the determining step comprises a first step comprising determining, based on said measuring, an initial amount of the determined gas in said headspace.

4. The method according to claim 3, wherein the gas mixture releasing step comprises a second step, following the first step, comprising releasing the gas mixture dissolved in the liquid, the measuring step comprises a second step comprising measuring an amount of the determined gas in the gas mixture released during said first and second steps of the gas mixture releasing step, and the determining step comprises a second step comprising determining, based on said measuring, an initial total amount of the determined gas in the sealed container.

5. The method according to claim 4, wherein to release the gas mixture from the liquid during said second step of the gas mixture releasing step, the liquid is subjected to vibrations.

6. The method according to claim 1, wherein the determined gas is oxygen.

7. The method according to claim 1, wherein the liquid is a carbonated beverage.

8. A method for measuring an amount of a determined gas in a sealed container containing a liquid in which a gas mixture is dissolved, comprising the steps of:
   piercing the sealed container;
   releasing the gas mixture from the pierced container;
   measuring an amount of the determined gas in the released gas mixture;
   determining, based on said measuring, an initial amount of the determined gas in the sealed container; and
   injecting an anti-foam agent into the pierced container before, during, or before and during the gas mixture releasing step,
   wherein the determining step comprises integrating over time the product of a measured flow rate of the released gas mixture and a measured partial pressure of the determined gas in the released gas mixture.

9. A method for measuring an amount of a determined gas in a sealed container containing a liquid in which a gas mixture is dissolved, comprising the steps of:
   piercing the sealed container;
   releasing the gas mixture from the pierced container;
   measuring an amount of the determined gas in the released gas mixture;
   determining, based on said measuring, an initial amount of the determined gas in the sealed container; and
   injecting an anti-foam agent into the pierced container before, during, or before and during the gas mixture releasing step,
   wherein the gas mixture releasing step comprises a first step comprising releasing the gas mixture from a headspace of the pierced container and a second step, following the first step, comprising releasing the gas mixture dissolved in the liquid,
   wherein the measuring step comprises a first step comprising measuring an amount of the determined gas in the gas mixture released from the headspace and a second step comprising measuring an amount of the determined gas in the gas mixture released during said first and second steps of the gas mixture releasing step, and
   wherein the determining step comprises a first step comprising determining, based on said measuring, an initial amount of the determined gas in said headspace and a second step comprising determining, based on said measuring, an initial total amount of the determined gas in the sealed container,
   wherein the second step of the determining step comprises integrating over time the product of a measured flow rate of the released gas mixture and a measured partial pressure of the determined gas in the released gas mixture.

10. A method for measuring an amount of a determined gas in a sealed container containing a liquid in which a gas mixture is dissolved, comprising the steps of:
    piercing the sealed container;
    releasing the gas mixture from the pierced container;
    measuring an amount of the determined gas in the released gas mixture;
    determining, based on said measuring, an initial amount of the determined gas in the sealed container; and
    injecting an anti-foam agent into the pierced container before, during, or before and during the gas mixture releasing step,
    wherein the gas mixture releasing step comprises a first step comprising releasing the gas mixture from a headspace of the pierced container and a second step, following the first step, comprising releasing the gas mixture dissolved in the liquid,
    wherein the measuring step comprises a first step comprising measuring an amount of the determined gas in the gas mixture released from the headspace and a second step comprising measuring an amount of the determined gas in the gas mixture released during said first and second steps of the gas mixture releasing step, and
    wherein the determining step comprises a first step comprising determining, based on said measuring, an initial amount of the determined gas in said headspace and a second step comprising determining, based on said measuring, an initial total amount of the determined gas in the sealed container,
    wherein between the first and second steps of the gas mixture releasing step the gas mixture release is interrupted for a determined time interval, the method further comprising the steps of obtaining a state of equilibrium between a liquid phase and a gaseous phase in the container in said time interval and determining an amount of another gas in the container by measuring an equilibrium temperature and an equilibrium total pressure in the container.

11. The method according to claim 10, wherein the step of determining said amount of said other gas comprises performing a calculation which involves the measured equilibrium temperature, the measured equilibrium total pressure and a measured percentage of said other gas in the gas mixture released.

12. The method according to claim 10, wherein said other gas is carbon dioxide.

13. A method for measuring an amount of a determined gas in a sealed container containing a liquid in which a gas mixture is dissolved, comprising the steps of:
    piercing the sealed container;
    releasing the gas mixture from the pierced container;
    measuring an amount of the determined gas in the released gas mixture;
    determining, based on said measuring, an initial amount of the determined gas in the sealed container;
    injecting an anti-foam agent into the pierced container before, during, or before and during the gas mixture releasing step,
    detecting when foam reaches a determined point in a gas releasing circuit connected to the pierced container; and
    stopping the gas mixture release when said detection occurs.

14. A device for measuring an amount of a determined gas in a sealed container containing a liquid in which a gas mixture is dissolved, comprising:
    a piercing mechanism configured to pierce the sealed container;
    a releasing mechanism configured to release the gas mixture from the pierced container;
    a sensor configured to measure an amount of the determined gas in the released gas mixture;
    means for determining, based on said measuring, an initial amount of the determined gas in the sealed container; and an injecting mechanism configured to inject an anti-foam agent into the pierced container, wherein said injecting mechanism comprises a first opening in the piercing mechanism; a second opening in the piercing mechanism, said second opening being closer to a piercing tip of said piercing mechanism than said first opening; a path connecting the first and second openings within the piercing mechanism; and a pump connected to the first opening for providing said anti-foam agent.

15. The device according to claim 14, wherein said determining means are in the form of a control unit which controls the gas mixture releasing means.

16. A device for measuring an amount of a determined gas in a sealed container containing a liquid in which a gas mixture is dissolved, comprising:

a piercing mechanism configured to pierce the sealed container;

a releasing mechanism configured to release the gas mixture from the pierced container;

a sensor configured to measure an amount of the determined gas in the released gas mixture;

means for determining, based on said measuring, an initial amount of the determined gas in the sealed container; and an injecting mechanism configured to inject an anti-foam agent into the pierced container, wherein said determining means are in the form of a control unit which controls the gas mixture releasing mechanism, and wherein the control unit is configured to perform a method for measuring an amount of a determined gas in a sealed container containing a liquid in which a gas mixture is dissolved, comprising the steps of:

piercing the sealed container;

releasing the gas mixture from the pierced container;

measuring an amount of the determined gas in the released gas mixture;

determining, based on said measuring, an initial amount of the determined gas in the sealed container; and injecting an anti-foam agent into the pierced container before, during, or before and during the gas mixture releasing step, wherein the determining step comprises integrating over time the product of a measured flow rate of the released gas mixture and a measured partial pressure of the determined gas in the released gas mixture.

17. A device for measuring an amount of a determined gas in a sealed container containing a liquid in which a gas mixture is dissolved, comprising:

a piercing mechanism configured to pierce the sealed container;

a releasing mechanism configured to release the gas mixture from the pierced container;

a sensor configured to measure an amount of the determined gas in the released gas mixture;

means for determining, based on said measuring, an initial amount of the determined gas in the sealed container; and an injecting mechanism configured to inject an anti-foam agent into the pierced container, wherein said determining means are in the form of a control unit which controls the gas mixture releasing means; and wherein said device further comprises means for detecting when foam reaches a determined point in said gas mixture releasing mechanism, said control unit being configured to stop the gas mixture release when said detection occurs.

18. A device for measuring an amount of a determined gas in a sealed container containing a liquid in which a gas mixture is dissolved, comprising:

a piercing mechanism configured to pierce the sealed container;

a releasing mechanism configured to release the gas mixture from the pierced container;

a sensor configured to measure an amount of the determined gas in the released gas mixture;

means for determining, based on said measuring, an initial amount of the determined gas in the sealed container; and an injecting mechanism configured to inject an anti-foam agent into the pierced container, wherein said piercing mechanism comprises a piercing tip which has at least one radial protuberance for forming at least one gas path at a periphery of a hole pierced into the sealed container, permitting the gas mixture to get out of the pierced container despite the piercing means passing through the pierced hole.

19. A device according to claim 18, wherein a temperature sensor is provided within the piercing tip.

* * * * *